(12) United States Patent
Lee

(10) Patent No.: US 12,414,781 B2
(45) Date of Patent: Sep. 16, 2025

(54) CERVICAL SPINE ENDPLATE PREPARATION APPARATUS

(71) Applicant: THE CATHOLIC UNIVERSITY OF KOREA INDUSTRY-ACADEMIC COOPERATION FOUNDATION, Seoul (KR)

(72) Inventor: Hong Jae Lee, Daejeon (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 313 days.

(21) Appl. No.: 18/265,819

(22) PCT Filed: Dec. 1, 2021

(86) PCT No.: PCT/KR2021/018041
§ 371 (c)(1),
(2) Date: Jun. 7, 2023

(87) PCT Pub. No.: WO2022/124691
PCT Pub. Date: Jun. 16, 2022

(65) Prior Publication Data
US 2024/0050106 A1    Feb. 15, 2024

(30) Foreign Application Priority Data
Dec. 8, 2020   (KR) .................. 10-2020-0170488

(51) Int. Cl.
*A61B 17/16* (2006.01)
*A61F 2/46* (2006.01)
*A61F 2/30* (2006.01)

(52) U.S. Cl.
CPC ........ *A61B 17/1671* (2013.01); *A61F 2/4611* (2013.01); *A61F 2002/30622* (2013.01)

(58) Field of Classification Search
CPC .................................................. A61B 17/1671
See application file for complete search history.

(56) References Cited

U.S. PATENT DOCUMENTS 6,443,956 B1 *   9/2002   Ray .................... A61B 17/1671
                                                    606/80
2004/0092941 A1 * 5/2004  Jansen .............. A61B 17/1671
                                                    606/84
(Continued)

FOREIGN PATENT DOCUMENTS

KR        10-2106023  B1        4/2020

OTHER PUBLICATIONS

International Search Report for PCT/KR2021/018041 dated Mar. 21, 2022.

*Primary Examiner* — Christian A Sevilla
(74) *Attorney, Agent, or Firm* — Sughrue Mion, PLLC

(57) ABSTRACT

A cervical spine endplate preparation apparatus is provided. To this end, the present invention comprises: a handle part having a handle to be held by hand and a leading rod extending from the handle in the length direction and for guiding to a space inside the spine of a part to be operated on; a rotating shaft part having an adjustment grip, which generates a driving force by means of rotation by hand, and a rotating shaft passing through the inside of the handle and leading rod; and a shaver part which has a case, provided on the leading rod and inserted into the space of the spine, and a shaver installed inside the case and mating with the rotating shaft to rotate by means of the driving force of the adjustment grip, and having a part of a blade exposed to the top of the case and rotating.

9 Claims, 8 Drawing Sheets

(56) References Cited

U.S. PATENT DOCUMENTS

| | | |
|---|---|---|
| 2005/0149192 A1* | 7/2005 | Zucherman ........ A61B 17/1671 |
| | | 623/17.11 |
| 2014/0121773 A1 | 5/2014 | Patel et al. |
| 2015/0182234 A1* | 7/2015 | Mahoney ........... A61B 17/1642 |
| | | 606/79 |
| 2019/0142603 A1 | 5/2019 | Tanaka |
| 2019/0343655 A1* | 11/2019 | Bruffey ................. A61F 2/4611 |
| 2020/0281743 A1 | 9/2020 | Jimenez et al. |

* cited by examiner

CERVICAL SPINE ENDPLATE PREPARATION APPARATUS

CROSS REFERENCE TO RELATED APPLICATIONS

This application is a National Stage of International Application No. PCT/KR2021/018041 filed Dec. 1, 2021, claiming priority based on Korean Patent Application No. 10-2020-0170488 filed Dec. 8, 2020, the entire disclosures of which are incorporated herein by reference.

TECHNICAL FIELD

The present invention relates to a cervical spine endplate preparation apparatus.

BACKGROUND ART

Basically, the basic purpose of modern spine surgery is decompression of compressive offending pathology and stability restoration, and spinal fusion surgery for stability restoration is also very important for the cervical spine where motion preservation surgery such as TDR is successfully performed.

The spinal fusion surgery is basically performed in the form of interbody fusion, and proper (fast, micro motion and no deformation) fusion of a vertebral body serving as a fusion bed and an interbody cage is an important factor in determining the patient's prognosis.

Permanent stability is due to bony fusion.

When the permanent stability fails, additional posterior cervical foraminotomy is often performed due to radiculopathy caused by subsidence (subsidence of the cage into the vertebral body).

In the case of the cervical spine, it is important to accurately remove the hypertrophied uncovertebral joint and insert a cage according to the degree of the accurate removal.

In the case of a ceramic cervical cage, especially a bio-ceramic cage that reacts with the bone, for stable fusion of the bone and a ceramic material, the cage needs to be positioned between the bone and the material without micro-movement to be fixed in an optimal position between the vertebrae.

To this end, bone-work should be performed between the vertebrae as much as possible in the same shape as the cage, and this process is called end-plate preparation.

This process uses a drilling and a curette, but excessive decortication may cause subsidence (subsidence into the vertebral body of the cage), and in the opposite case, fusion delay or failure may be caused.

This technology is a surgical apparatus (device) designed to make such end-plate preparation more precise and efficient.

This technology is a technology capable of maximizing a bone fusion function by minimizing the micro-movement that may occur after surgery by performing the end-plate preparation in the same shape as the cage through this apparatus.

The apparatus is widely used in medical treatment, especially in surgery and surgical procedures, and has various shapes depending on the purpose.

A curette with sharp edges is used to curette tissues or bones, and the basic shapes are a double-headed curette and a single-headed curette.

In addition, in the shape of a spoon, the curette has a hollow spoon called a JOMW uterine curette and a SIMS uterine curette as well as a circle and an ellipse.

There are various sizes in the size of a spoon and the length of a handle.

A curette with blunt edges is called a blunt curette. These curettes approach a surgical site at a location of the disc in the spine, and the curette is subjected to a preparation to remove the disc at the location and install an end plate by a rotational force.

DISCLOSURE

Technical Problem

An object of the present invention is to enable an operator to perform an end-plate preparation of a vertebral body in a desired shape by removing a disc and installing an end plate in a narrow space of the spine.

Another object of the present invention is to achieve an exposed height of a shaver by manipulating a shaver part in the end-plate preparation of the vertebral body.

Technical Solution

There is provided a cervical spine endplate preparation apparatus.

To this end, the present invention includes: a handle part having a handle to be held by hand and a leading rod extending from the handle in the length direction and for guiding to a space inside the spine of a part to be operated on; a rotating shaft part having an adjustment grip, which generates a driving force by means of rotation by hand, and a rotating shaft passing through the inside of the handle and leading rod; and a shaver part which has a case, provided on the leading rod and inserted into the space of the spine, and a shaver installed inside the case and mating with the rotating shaft to rotate by means of the driving force of the adjustment grip, and having a part of a blade exposed to the top of the case and rotating.

Advantageous Effects

According to the present invention, as the rotatable shaver rotates in an axial direction of the entire structure, the blade of the shaver contacts the upper endplate of the internal space of the spine to accurately perform bone-work.

In addition, according to the present invention, the shaft is connected to the shaver part to enable the rotation of the shaver, and a handle is attached to the distal end of the shaft, so that there is an advantage that the operator can arbitrarily operate the blades of the shaver by rotating the handle, and can select the exposure degree of the blade.

MODES OF THE INVENTION

Figure 1:
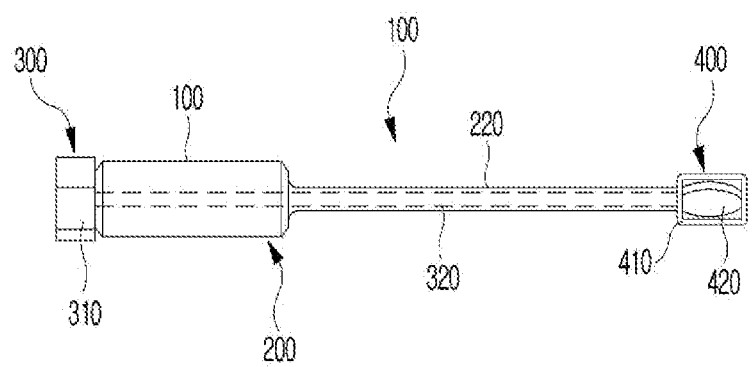
FIG. 1 is a plane state diagram to which the present invention is applied.
Figure 2:
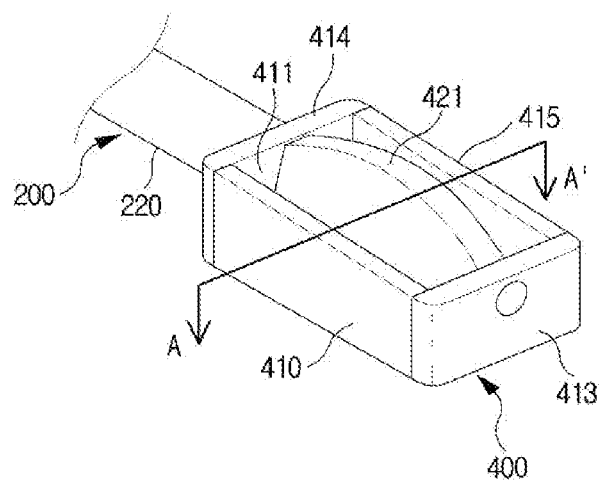
FIG. 2 is a perspective view of a shaver part of the present invention.

FIG. 1 is a plane state diagram to which the present invention is applied and FIG. 2 is a perspective view of a shaver part of the present invention.

A cervical spine endplate preparation apparatus 100 of the present invention is formed with a handle part 200 having a leading rod 220 that extends in the length direction from a handle 210 formed to be held by hand and guides to a space inside the spine of a part to be operated on.

In addition, the cervical spine endplate preparation apparatus 100 is formed with a rotating shaft part 300 having an adjustment grip 310, which generates a driving force by means of rotation by hand, and a rotating shaft 320 passing through the inside of the handle 210 and the leading rod 220.

A case 410 provided on the leading rod 220 and inserted into the space of the spine to cut the installation site mates with the rotating shaft 320 installed inside the case 410 to rotate by means of the driving force of the adjustment grip 310.

A shaver part 400 having a part of a blade 421 exposed to the top of the case 410 and rotating is formed to be used for forming an installation site of so-called intervertebral body.

Figure 3:
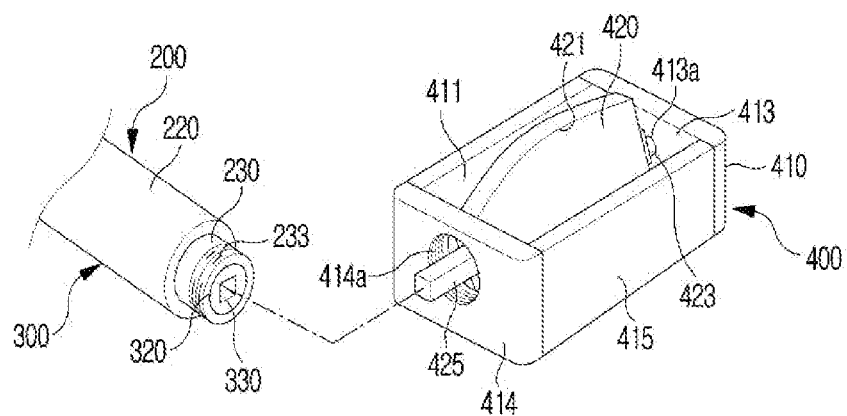
FIG. 3 is a perspective view of a state in which a rotating shaft part and the shaver part of the present invention are separated from each other.

FIG. 3 is a perspective view of a state in which the rotating shaft part and the shaver part of the present invention are separated from each other, and a structure of coupling the handle part 200 held by hand of a medical staff and the shaver part 400 that performs cutting in an operating site of the cervical spine will be described.

A fastening end 230 having a smaller diameter than the leading rod is formed at the end of the leading rod 220 formed in the length direction from one side of the handle 210 of the handle part 200 and a screw part 233 is formed on the outer diameter of the fastening end 230 so that the case 410 of the shaver part 400 is coupled and separated.

The leading rod 220 of the handle part 200 is formed in a hollow tube with a thin diameter to have an assembled state in which the rotating shaft 320 of the rotating shaft part 300 is inserted into the hollow tube at the position of the handle 210 to reach a tip of the leading rod extending from the handle.

The adjustment grip 310 for forming a driving force is installed at one end of the rotating shaft 320 inserted into the hollow tube of the leading rod, and a shaft groove 330 for transmitting the driving force to the shaver part 400 is formed at the other end exposed from the tip of the leading rod 220.

The shaft groove 33 is preferably formed as a rectangular concave groove for assembly with the shaver part 400 and transmission of the driving force.

The shaver part 400 has the case 410 having a frame shape with a hollow space to be coupled at the fastening end 233 of the leading rod 220, and a shaver 420 installed inside the case 410 and mating with the rotating shaft 320.

The case 410 is configured so that for easy and stable insertion into the internal space of the cervical spin, a lower surface becomes horizontal while an upper surface slopes from the rear to the front, a support hole 413a for installing the shaver 420 is perforated in the front surface of the frame of the case 410, and a fixing hole 414a for coupling at the fastening end 230 of the leading rod 220 is perforated in the rear surface thereof.

When the height of a rear surface 414 is greater than that of a front surface 413 forming the case 410, the inclined shape of the case 410 is formed to the front end from the rear end of a side surface 415 connected between the front surface and the rear surface, and an inclined shape of the side surface 415 is formed in a curved or straight line.

In addition, the support hole 413a for rotating and supporting the shaver 410 is formed in the front surface 413 of the case 410, and in the rear surface 414, the fixing hole 414a to which the fastening end 230 formed on the leading rod 220 of the handle part 200 is coupled is formed.

In addition, the shaver 420 installed inside the case 410 and rotated by a driving force is formed in a thin plate shape of an appropriate size to be rotated in the space of the case.

The shaver 420 is formed with blades 421 on both sides, and both ends of the blade 421 have a convex arc shape for efficient cutting.

In forming the shaver 420, a protruding shaft 425 mating with the shaft groove 330 formed at the end of the rotating shaft 320 is formed at one end of the shaver 420 formed in a thin plate shape, and a support shaft 423 is formed at the other end to be assembled to the case 410 to be rotated and supported.

While the shaver part 400 couples the fixing hole 410a formed in the case 410 to the fastening end 230 formed at the end of the leading rod 220, the screw threads and the screw grooves formed in the fastening end 230 and the fixing hole 410a are mutually fastened to each other.

In using the cervical spine endplate preparation apparatus 100 assembled as described above, while the handle 210 of the handle part 200 is gripped, the shaver part 400 coupled to the tip of the leading rod 220 is moved to the operating site to allow the case 410 to be inserted into the operating site, that is, the space inside the cervical spine through the cutting portion.

At this time, the case 410 of the shaver part 400 to be inserted has an inclined upper end and a horizontal lower end to be easily inserted into the internal space of the cervical spine.

When the entering state of the case 410 into the internal space of the cervical spine is confirmed through an operating device, the adjustment grip 310 of the rotating shaft part 300 provided on one side of the handle 210 is operated by the other hand.

When the adjustment grip 310 is operated, the rotating shaft 320 rotates inside the handle 210 of the handle part 200, and at this time, since the rotation is transferred to the shaver 420 of the shaver part 400 installed in the case 410 coupled to the fastening end 230, the disc and the installation site are cut by a rotational motion in the cervical spine space.

After the installation site is cut, a separate intervertebral body is inserted into the corresponding space.

Figure 4:
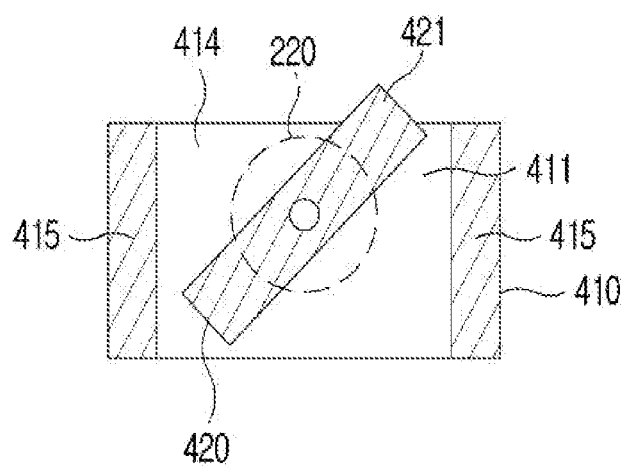
FIG. 4 is a cross-sectional view of FIG. 3 taken along line A-A'.
Figure 5:
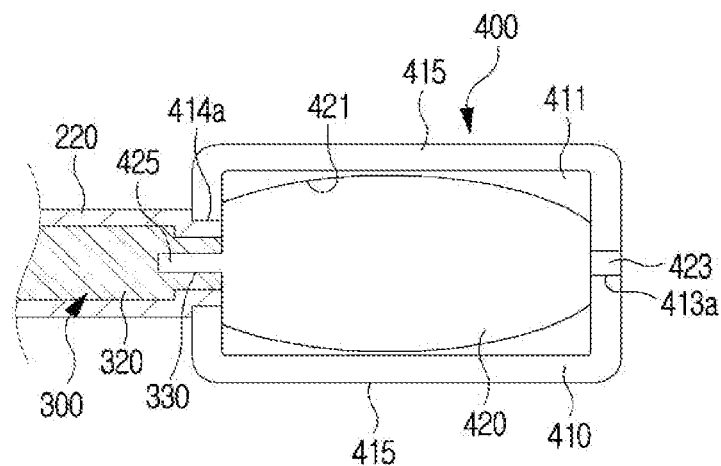
FIG. 5 is a top cross-sectional view of the shaver part of the present invention.
Figure 6:
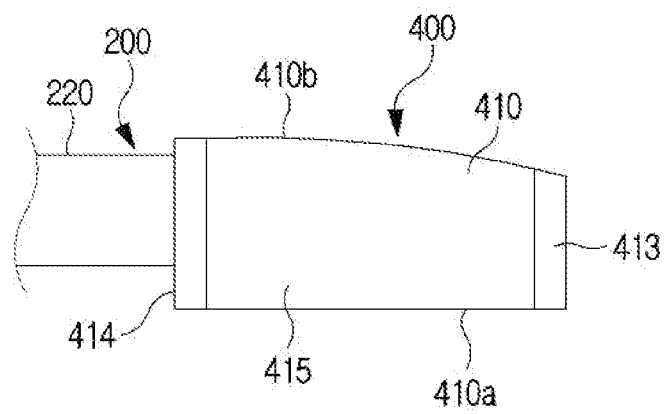
FIG. 6 is a side state diagram of the shaver part of the present invention.

In the cutting state of the shaver 420 in the case 410, while the front surface 413 is formed at a height lower than the rear surface 414 as shown in FIG. 6, the shaver 420 is installed eccentrically upward in the case 410 as shown in FIG. 4 so that the blades 421 at both ends are partially exposed only to the inclined upper end of the case 410 when rotating the shaver 420.

As such, while the shaver 420 is partially exposed to the upper end of the case 410 of the shaver part 400, the rotation may make precisely and smoothly the endplate preparation for installing the end plate of the body in the internal space of the spine where the work space is narrow.

As described above, since the endplate preparation for installing the end plate of the body in the internal space of the spine is precisely performed, in order to improve the preparation efficiency, the size of the shaver part 400 coupled to the fastening end 230 is formed in stages in the form of 3 mm, 4 mm, 5 mm, and 6 mm to perform cervical spine surgery while selectively replacing the shaver part 400 with a size suitable for the preparation form.

In order to easily and safely couple the fastening end 230 and the case 410 of the shaver part 400, the screw part 233 is formed on the fastening end 230, and the screw groove 414a is formed in the fixing hole 414a perforated in the rear surface 414 of the case 410, so as to be coupled and separated in the form of a screw.

Exemplary Embodiment 1

The coupling and separation of the rotating shaft part 300 and the shaver part 400 may be configured as an exemplary embodiment in an insertion fastening method rather than a screw fastening method.

Figure 7:
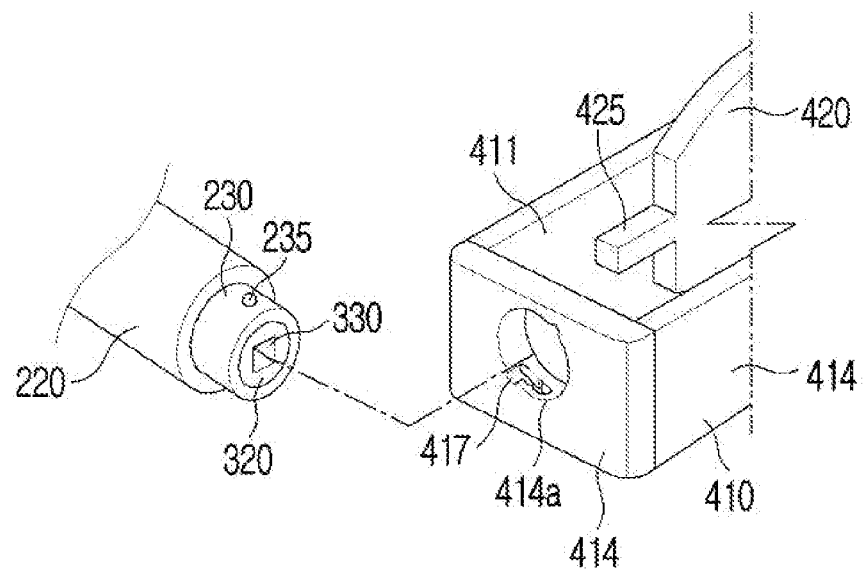
FIG. 7 is a separated perspective view of an exemplary embodiment of coupling the rotating shaft part and the shaver part of the present invention.
Figure 8:
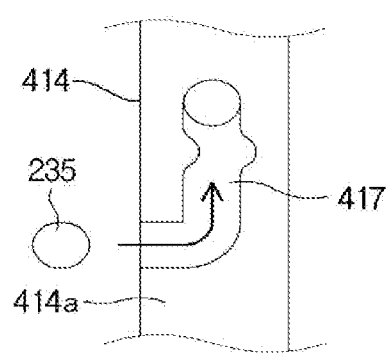
FIG. 8 is a plan view of an exemplary embodiment of a coupling structure formed in a case of the present invention.
Figure 9:
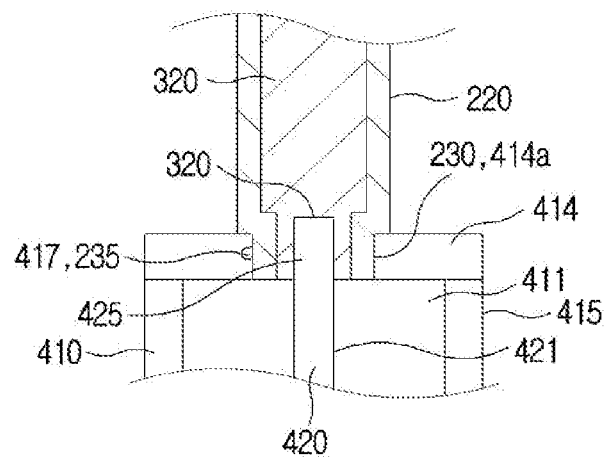
FIG. 9 is a cross-sectional view showing a state in which the rotating shaft part and the shaver part of the present invention are coupled with each other in another coupling structure.
Figure 10:
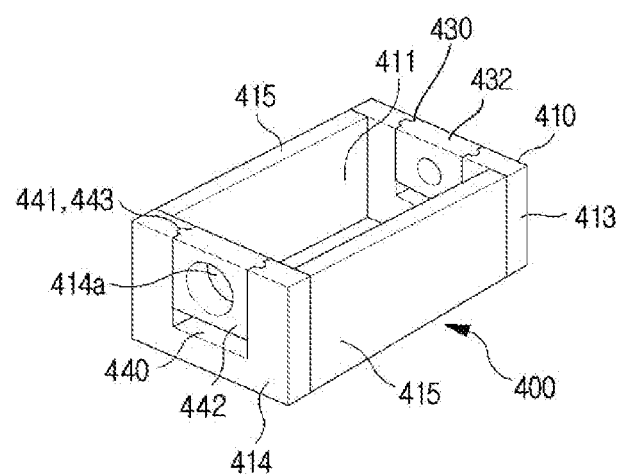
FIG. 10 is a perspective view showing a shaver exposure height adjustment structure provided in the case of the present invention.
Figure 11:
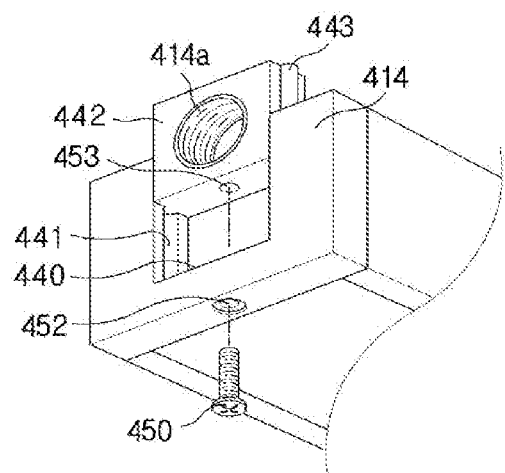
FIG. 11 is a perspective view of the shaver exposure height adjustment structure provided in the case of the present invention when viewed from the bottom.
Figure 12:
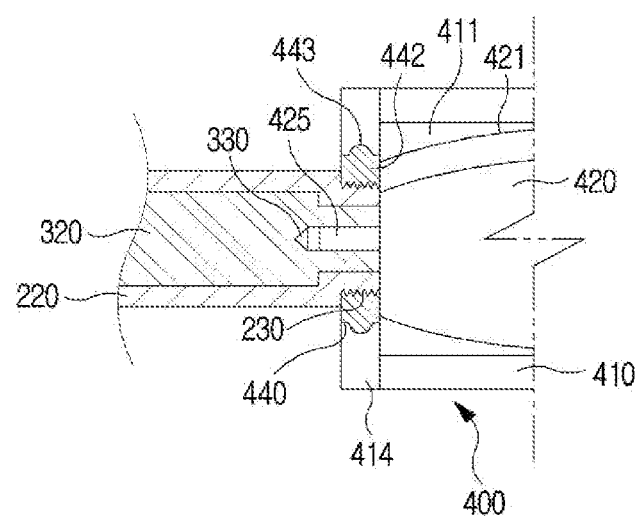
FIG. 12 is a top cross-sectional view showing the shaver exposure height adjustment structure provided in the case of the present invention.
Figure 13:
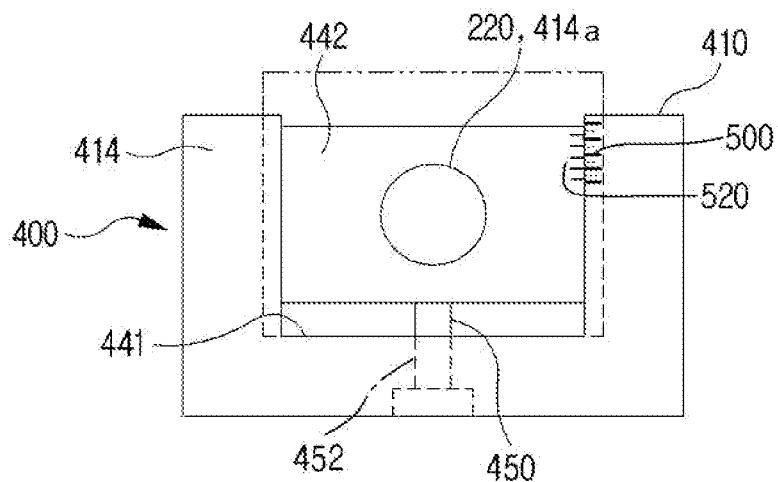
FIG. 13 is a state view of the shaver exposure height adjustment structure of the present invention when viewed in a rotating shaft direction.
Figure 14:
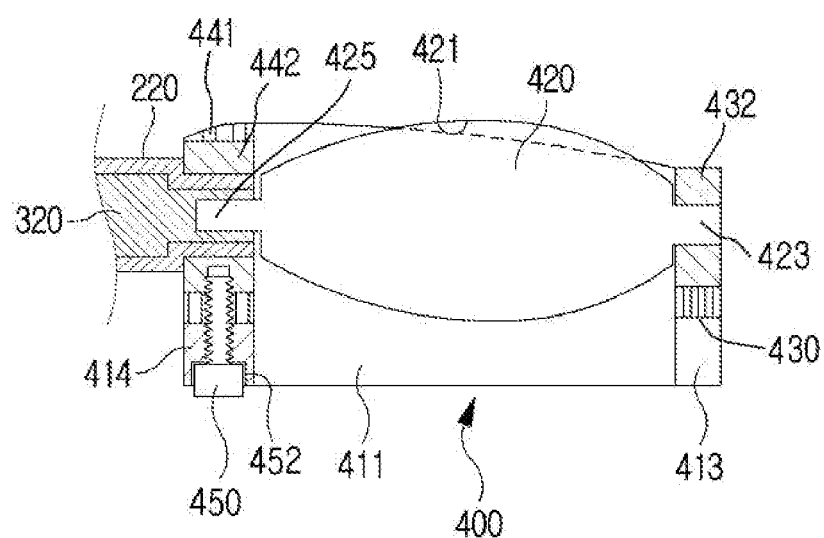
FIG. 14 is a state view of the shaver exposure height adjustment structure of the present invention when viewed in a length direction from the case side.
Figure 15:
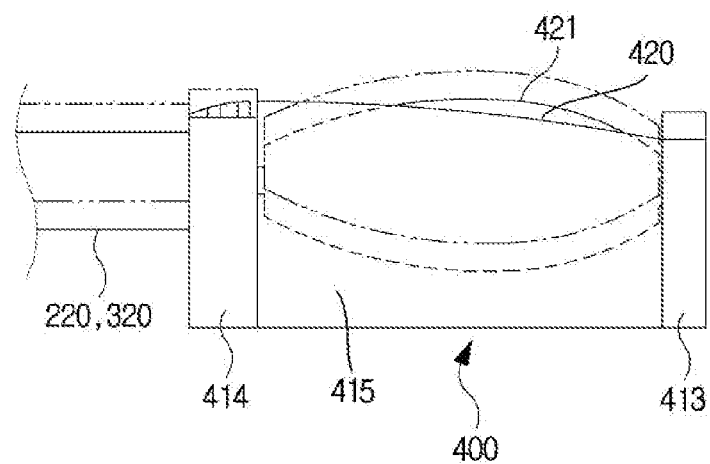
FIG. 15 is a side view showing a state in which the exposure height of the shaver is adjusted in the present invention.

An exemplary embodiment of the insertion fastening method shows a separation state for the coupling of the rotating shaft part and the shaver part of FIG. 7 and a plan state of the coupling structure formed in the case of FIG. 8.

The cervical spine endplate preparation apparatus 100 of the present invention has a circular protrusion 235 formed in the rotating shaft part 300 and the shaver part 400 and protruding from the fastening end 230 provided in the leading rod 220 of the handle part 200 in the insertion fastening method, and a locking groove 417 for inserting the circular protrusion 235, guiding the coupling, and locking in the fixing hole 414a formed in the case 410 of the shaver part 400.

In the insertion fastening method formed as described above, while coupling the fixing hole 414a formed in the case 410 of the shaver part 400 to the fastening end 230 of the leading rod 220, the circular protrusion 235 protruding from the fastening end 230 is inserted and twisted into the lock groove 417 formed in the fixing hole 414a of the case 410.

The circular protrusion 235 is inserted and guided into the lock groove 417 and locked to the lock groove 417, so that the insertion-guided locking operation of the circular protrusion 235 and the lock groove 417 may easily replace the shaver part 400 rather than the screw part and maintain a stable installation state after replacing.

Exemplary Embodiment 2

Another exemplary embodiment of the rotating shaft part 300 and the shaver part 400 may be configured in a slider adjustment method other than the insertion fastening method.

In the present invention, another slider adjustment method for the rotating shaft part 300 and the shaver part 400 will be illustrated in detail in FIGS. 10 to 15.

The shaver part 400 includes first and second slide holes 430 and 440 formed by cutting the front surface 413 and the rear surface 414 of the case 410, and is assembled in the first and second slide holes 430 and 440.

The shaver part 400 consists of first and second blocks 432 and 442 in which the leading rod 220 and the shaver 420 are installed, a through hole 452 perforated from the lower surface of the case 410, and an adjustment screw 450 inserted into the through hole 452 and screwed to the second block 442.

The shaver part 400 is formed with scales 520 on the front surface 413 and the rear surface 414 of the case 410 where the first and second slide holes 430 and 440 are formed. In addition, the scales 520 are also formed on the first and second blocks 432 and 442 so that the protruding heights of the first and second blocks 432 and 442 are selectively controlled at the upper end of the case 410.

According to Exemplary Embodiment, in the endplate preparation for installing the end plate of the body in the internal space of the cervical spine where the preparation space is narrow, the first block 432 and the second block 442 are moved in the first slide hole 430 and the second slide hole 440 by adjusting the adjustment screw 450.

Since the position of the shaver 420 is adjusted to the height exposed to the upper end in the space 411 of the case 410, the replacement of the shaver part 400 is not required.

Moving scales 520 are formed in the first block 432 and the second block 42 that are moved by the adjustment of the adjustment screw 450, and corresponding reference scales 500 are also formed around the first slide hole 430 of the front surface 413 and the second slide hole 440 of the rear surface 414 of the case 410. Accordingly, it is possible to set the protruding height of the block, that is, the exposure height of the shaver 420, which can select the amount of cutting, according to a surgical situation.

The invention claimed is:

1. A cervical spine endplate preparation apparatus comprising:
    a handle part having a handle to be held by hand and a leading rod extending from the handle in a length direction and for guiding to a space inside the spine of a part to be operated on;
    a rotating shaft part having an adjustment grip, which generates a driving force by means of rotation by hand, and a rotating shaft passing through an inside of the handle and leading rod; and
    a shaver part which has a case, provided on the leading rod and capable of being inserted into the space of the spine, and a shaver installed inside the case and mating with the rotating shaft to rotate by means of the driving force of the adjustment grip, and the shaver having a part of a blade exposed to a top of the case, the shaver being configured to rotate.

2. The cervical spine endplate preparation apparatus of claim 1, wherein in the handle part, a fastening end having a smaller diameter than the leading rod is formed at an end of the leading rod and threads are formed on an outer diameter of the fastening end.

3. The cervical spine endplate preparation apparatus of claim 1, wherein:
the rotating shaft is capable of being inserted to a tip of the leading rod through the handle;
the rotating shaft part includes an adjustment grip formed at one end of the rotating shaft to form a driving force on the handle part; and
the rotating shaft part includes a shaft groove formed at an end of the rotating shaft capable of being exposed at the tip of the leading rod, the shaft groove being configured to be coupled to and to be separated from the shaver part.

4. The cervical spine endplate preparation apparatus of claim 1, wherein the shaver part includes the case having a frame with a hollow space, wherein the shaver part is capable of being to be detached from the leading rod, wherein a lower surface of the case is horizontal while an upper surface of the case is inclined from the rear to the front, wherein a support hole for the shaver is perforated in a front surface of the frame, and a fixing hole for the leading rod is perforated in a rear surface of the frame.

5. The cervical spine endplate preparation apparatus of claim 1, wherein the shaver is formed in a thin plate shape in an appropriate size to be rotated in a space of the case, wherein a protruding shaft of the shaver capable of mating with a shaft groove of the rotating shaft is formed at one end of the shaver, and a support shaft is formed at the other end of the shaver to be rotated and supported on the case, and
wherein blades are formed on both sides of the shaver, each blade having a convex arc shape.

6. The cervical spine endplate preparation apparatus of claim 1, wherein the leading rod of the handle part includes:
a circular protrusion formed on a fastening end of the leading rod, and a lock groove is formed on a fixing hole formed in the case of the shaver part to be inserted, coupled, and locked to the circular protrusion.

7. The cervical spine endplate preparation apparatus of claim 1, wherein the shaver installed in the case is capable of being rotated while a convex portion of the blade is exposed to an inclined upper end of the case.

8. The cervical spine endplate preparation apparatus of claim 1, wherein the shaver part includes:
first and second slide holes formed in a front surface and a rear surface of the case,
first and second blocks assembled with the first and second slide holes, the blocks being capable of being installed with the leading rod and the blade,
a through hole perforated from a lower surface of the case, and
an adjustment screw capable of being inserted into the through hole to be screwed to one of the blocks.

9. The cervical spine endplate preparation apparatus of claim 8, wherein the shaver part has scales formed on a front surface and a rear surface of the case where the first and second slide holes are formed, and scales are formed on the first and second blocks so that protruding heights of the blocks can be selectively controlled.

* * * * *